US012048507B2

(12) United States Patent
Abbosh et al.

(10) Patent No.: US 12,048,507 B2
(45) Date of Patent: Jul. 30, 2024

(54) STROKE MONITORING

(71) Applicant: EMvision Medical Devices Ltd, Brisbane (AU)

(72) Inventors: Amin Abbosh, Brisbane (AU); Arman Afsari, Brisbane (AU)

(73) Assignee: EMVISION MEDICAL DEVICES LTD, Brisbane (AU)

( * ) Notice: Subject to any disclaimer, the term of this patent is extended or adjusted under 35 U.S.C. 154(b) by 507 days.

(21) Appl. No.: 17/310,853

(22) PCT Filed: Mar. 4, 2020

(86) PCT No.: PCT/AU2020/050201
§ 371 (c)(1),
(2) Date: Aug. 26, 2021

(87) PCT Pub. No.: WO2020/176940
PCT Pub. Date: Sep. 10, 2020

(65) Prior Publication Data
US 2022/0079443 A1 Mar. 17, 2022

(30) Foreign Application Priority Data
Mar. 4, 2019 (AU) .................................. 2019900703

(51) Int. Cl.
A61B 5/00 (2006.01)
A61B 5/0507 (2021.01)
(Continued)

(52) U.S. Cl.
CPC .......... A61B 5/0042 (2013.01); A61B 5/0037 (2013.01); A61B 5/0507 (2013.01);
(Continued)

(58) Field of Classification Search
CPC ... A61B 5/0042; A61B 5/0037; A61B 5/0507; A61B 5/4842; A61B 5/7203;
(Continued)

(56) References Cited

FOREIGN PATENT DOCUMENTS

CN 109589115 A * 4/2019 ............... A61B 5/05
WO WO 2011/100343 8/2011
(Continued)

OTHER PUBLICATIONS

Boverman, G. et al. 'Image registration for microwave tomography of the breast using priors from nonsimultaneous previous magnetic resonance images', IEEE Journal of Electromagnetics, RF and Microwaves in Medicine and Biology. 2018, vol. 2, No. 1, pp. 2-9.
(Continued)

Primary Examiner — Bo Joseph Peng
(74) Attorney, Agent, or Firm — Knobbe, Martens, Olson & Bear, LLP

(57) ABSTRACT

A computer-implemented process for continuous monitoring of a brain stroke during a critical rehabilitation period, the process including the steps of: (i) accessing initial image data representing an initial image of a subjects brain containing a stroke region; (ii) accessing scattering parameter data representing microwaves scattered by the subjects brain and originating from a plurality of antennas disposed around the subjects brain; and (iii) processing the scattering parameter data and the initial image data using a gradient-free optimisation method to generate estimates of spatial dimensions of the stroke region within the subjects brain, wherein the initial image of the subjects brain is used as a priori information to improve the accuracy of the generated estimates, and the spatial dimensions of the stroke region are generated as global parameters of the gradient-free optimisation method.

19 Claims, 9 Drawing Sheets

(51) Int. Cl.
*G06T 7/00* (2017.01)
*G06T 7/60* (2017.01)
*G16H 30/40* (2018.01)
*A61B 5/0522* (2021.01)
*A61B 5/055* (2006.01)
*A61B 6/00* (2006.01)

(52) U.S. Cl.
CPC .......... *A61B 5/4842* (2013.01); *A61B 5/7203* (2013.01); *G06T 7/0012* (2013.01); *G06T 7/60* (2013.01); *G16H 30/40* (2018.01); *A61B 5/0522* (2013.01); *A61B 5/055* (2013.01); *A61B 6/488* (2013.01); *A61B 6/5247* (2013.01); *A61B 2505/09* (2013.01); *G06T 2207/10088* (2013.01); *G06T 2207/10116* (2013.01); *G06T 2207/30016* (2013.01)

(58) Field of Classification Search
CPC ....... A61B 5/0522; A61B 5/055; A61B 6/488; A61B 6/5247; A61B 2505/09; A61B 5/4094; A61B 5/7282; A61B 6/5217; A61B 6/501; A61B 5/05; A61B 5/4848; A61B 5/02007; A61B 5/489; A61B 6/504; A61B 2562/0228; A61B 2562/04; A61B 2576/026; A61B 5/4064; G06T 7/0012; G06T 7/60; G06T 2207/10088; G06T 2207/10116; G06T 2207/30016; G06T 2207/10081; G06T 7/0014; G06T 7/0016; G16H 30/40

See application file for complete search history.

(56) References Cited

FOREIGN PATENT DOCUMENTS

| WO | WO 2018/098387 | 5/2018 | |
|---|---|---|---|
| WO | WO 2018/223178 | 12/2018 | |
| WO | WO-2020047597 A1 * | 3/2020 | .......... A61B 5/0042 |
| WO | WO-2020047599 A1 * | 3/2020 | .......... A61B 5/0042 |

OTHER PUBLICATIONS

Persson, M. et al. 'Microwave-Based Stroke Diagnosis Making Global Prehospital Thrombolytic Treatment Possible,' IEEE Transactions on Biomedical Engineering. 2014, vol. 61, No. 11, pp. 2806-2817.

Written Opinion of the Internationl Searching Authority, PCT/AU2020/050201, Dated Mar. 4, 2019, in 4 pages.

\* cited by examiner

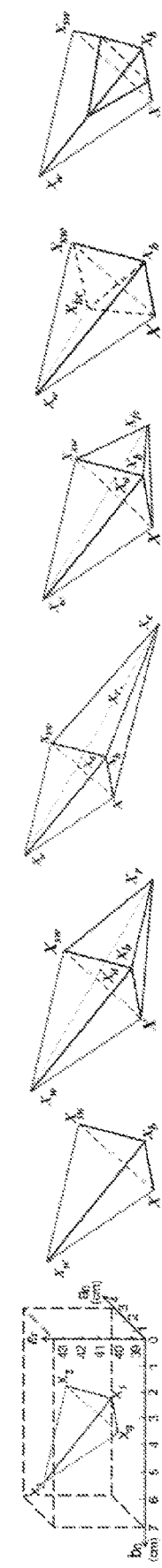

STROKE MONITORING

This application is a U.S. national phase application under 35 U.S.C. § 371 of international patent application No. PCT/AU2020/050201, filed on Mar. 4, 2020, and entitled "Stroke Monitoring," which claims priority to Australian patent application No. 2019900703, filed on Mar. 4, 2019, the entire contents of each of which are incorporated herein by reference.

TECHNICAL FIELD

The present invention relates to medical imaging, and in particular to an apparatus and process for continuous monitoring of a brain stroke during a critical rehabilitation period.

BACKGROUND

The World Health Organization defines stroke as a "neurological deficit of cerebrovascular cause that persists beyond 24 hours or is interrupted by death within 24 hours". This demonstrates the need to act swiftly so that treatment can be applied to reduce stroke severity, knowing that after around six hours following the onset of symptoms, the resulting lost brain functions become irreversible. However, such swift action is currently performed under partial medical blindness, because there is currently no stroke monitoring tool to efficiently measure the stroke "geometry" and its response to treatment.

The first six hours following the occurrence of a stroke is usually referred to as the "critical rehabilitation period" ("CRP"), which is defined as "the period in which the lost functions caused by stroke may be recoverable". Accordingly, medical treatment of stroke is performed immediately once a stroke has been diagnosed. The medical treatment, however, needs to include substantially continuous monitoring, especially during the CRP, to assess the effect of medication or other treatment on the "geometrical size" of the stroke, and provide corresponding medical adjustments (e.g., immediately changing to a different treatment, depending on the behavior of the stroke) if needed. Such a critical need, nevertheless, is not currently facilitated by currently available imaging modalities, for which an example is described in P. D. Schellinger et al., "Monitoring intravenous recombinant tissue plasminogen activator thrombolysis for acute ischemic stroke with diffusion and perfusion MRI," Stroke, vol. 31, no. 6, pp. 1318-1328, March 2000 ("Schellinger").

Geometrical Change of Stroke During the CRP

To demonstrate stroke behavior during the CRP, FIG. 1A shows an MRI-derived stroke model, three hours after symptoms onset, resembling the medical situation in Schellinger. The model is derived from an image generated by a 'stroke-MRI' imaging modality that is used in emergency situations. The main objective of this imaging modality is to merely reveal the severity of stroke, and consequently it typically possesses less specificity in comparison with conventional MRI images, which require longer computational times to generate.

FIGS. 1B and 1C represent two possible changes in the shape of the stroke of FIG. 1A during the CRP, five and a half hours after symptom onset. The enlargement of the stroke shown in FIG. 1B is usually referred to as "hypoperfusion", and is characterised by an inadequate oxygen supply to brain tissues due to the extension of the "clot"†, lowering the dielectric properties of the affected area to values that are 10-15% below the dielectric properties of the surrounding tissues. This situation occurs when a thrombolytic treatment (the process of breaking down the "clot" by injecting or directly delivering (using a catheter) a clot dissolving medicine to the affected area) is performed rather late, typically after four and a half hours from symptom onset, and acts oppositely to grow the stroke region, rather than shrink it as intended.

†During stroke, when the artery of brain bursts, the blood flooding into the surrounding tissues forms a clot after around 4 minutes. Hence, the affected area of the brain is already occupied by a clot upon patient arrival.

FIG. 1C, on the other hand, demonstrates the breakdown of the clot when thrombolytic treatment is performed in-time, typically within the first four hours following stroke onset. The geometrical changes of FIGS. 1B and 1C are different critical responses to the stroke treatment, but are currently undetectable due to the lack of an efficient stroke monitoring process.

Barriers Against the Real-Time Monitoring

The lack of a continuous monitoring technology originates from some intrinsic limitations of existing medical imaging modalities, mainly MRI and X-Ray. For instance, the bulky and static structure of MRI prevents its use as a continuous monitoring tool, because patients with severe stroke are normally in an emergency medical stage that precludes their repeated transferal between the intensive care unit (ICU) and the imaging unit for monitoring. Moreover, the ionizing effects of X-Rays and the genotoxic influence of MRI on the human body prevents these imaging modalities from being used to continuously expose the body to potentially unsafe doses of radiation.

In order to address these difficulties, electromagnetic tomography (EMT) has been introduced as a potential monitoring modality. EMT involves reconstructing the image of an unknown object from measurement data, typically in a form referred to in the art as an "S-matrix" or "scattering parameters". This imaging modality benefits from the EMT hardware being low-weight and thus portable and installable in every medical unit, including the ICU, and also from being safe as it does not cause the ionization and genotoxic effects of MRI and X-ray imaging modalities.

However, EMT suffers from some limitations compared to these well-established techniques. In particular, the diffraction effect and the presence of highly localized evanescent waves at sharp corners of human head tissues (particularly the rounded corners between the brain and cerebrospinal fluid as shown in FIG. 1A) are significant in the UHF (300 MHz to 3 GHz) and S (2-4 GHz) frequency bands where medical EMT is usually performed. Consequently, EMT images are geometrically coarse and do not accurately represent the actual shape of the object being imaged (e.g., the stroke region), although this is desirable for CRP monitoring.

For example, FIG. 1D is an EMT image showing the spatial distribution of relative permittivity ($\varepsilon_r$) for the example of FIG. 1A, as generated using eight imaging dipole antennas operating at 1.5 GHz. Even a cursory comparison with FIG. 1A demonstrates that the calculated image does not accurately represent the actual spatial distribution or dielectric properties of the stroke (the retrieved conductivity, denoted by $\sigma$, is excluded from demonstration because the corresponding retrieval accuracy for conductivity $\sigma$ is usually poorer than for the relative permittivity $\varepsilon_r$). In addition, the corresponding computational time required to generate a medical image by EMT is rather high. For example, the time is around 76 minutes to generate the image of FIG. 1D at a 15 dB signal-to-noise ratio (SNR) using a computer platform with an Intel Core™ i7-4790

CPU at 3.6 GHz and 16 GB of RAM. Hence, the diffraction effect, the presence of evanescent waves in the UHF and S bands, and the prohibitively high computational time required all exclude conventional EMT from being used for standalone stroke monitoring. As noted in Schellinger: "the need remains for a stroke imaging tool that is fast, has a sufficiently high sensitivity for detecting intracerebral hemorrhage (ICH) within the first 6 hours, and can identify the tissue at risk if present".

It is desired, therefore, to overcome or alleviate one or more difficulties of the prior art, or to at least provide a useful alternative.

SUMMARY

In accordance with some embodiments of the present invention, there is provided a computer-implemented process for continuous monitoring of a brain stroke during a critical rehabilitation period, the process including the steps of:
(i) accessing initial image data representing an initial image of a subject's brain containing a stroke region;
(ii) accessing scattering parameter data representing microwaves scattered by the subject's brain and originating from a plurality of antennas disposed around the subject's brain; and
(iii) processing the scattering parameter data and the initial image data using a gradient-free optimisation method to generate estimates of spatial dimensions of the stroke region within the subject's brain, wherein the initial image of the subject's brain is used as a priori information to improve the accuracy of the generated estimates, and the spatial dimensions of the stroke region are generated as global parameters of the gradient-free optimisation method.

In some embodiments, the spatial dimensions of the stroke region are initially determined by optimising the spatial dimensions of a first predetermined permittivity value of the stroke region and a second predetermined permittivity value for non-stroke regions of the subject's brain.

In some embodiments, the spatial dimensions and relative permittivity of the stroke region are generated as global parameters of the gradient-free optimisation method.

In some embodiments, the shape of the stroke region is approximated by overlapping ellipses in a two-dimensional plane, and the spatial dimensions of the stroke region are determined by determining the spatial dimensions of the overlapping ellipses.

In some embodiments, the overlapping ellipses have minor axes with fixed spatial dimensions, and the spatial dimensions of the overlapping ellipses are determined as two parameters corresponding to major axes of the overlapping ellipses. In some other embodiments, the spatial dimensions of the stroke region are determined by determining four geometrical parameters.

In some embodiments, the process includes repeating steps (ii) and (iii) at successive times to monitor growth or shrinkage of the stroke region over time.

The gradient-free optimisation method may be a Nelder-Mead gradient-free optimisation method.

The initial image of the subject's brain may be generated by magnetic resonance imaging or x-ray imaging or electromagnetic tomography imaging.

In accordance with some embodiments of the present invention, there is provided an apparatus for continuous monitoring of a brain stroke during a critical rehabilitation period, the apparatus including:
a memory;
at least one processor; and
at least one computer-readable storage medium having stored thereon instructions that, when executed by the at least one processor, cause the at least one processor to execute the steps of:
(i) accessing initial image data representing an initial image of a subject's brain containing a stroke region;
(ii) accessing scattering parameter data representing microwaves scattered by the subject's brain and originating from a plurality of antennas disposed around the subject's brain; and
(iii) processing the scattering parameter data and the initial image data to estimate spatial dimensions of the stroke region within the subject's brain, wherein the initial image of the subject's brain is used as a priori information to improve the accuracy of the determination, and the spatial dimensions of the stroke region are determined as global parameters of a gradient-free optimisation method.

In some embodiments, the spatial dimensions of the stroke region are initially determined by optimising the spatial dimensions of a first predetermined permittivity value of the stroke region and a second predetermined permittivity value for non-stroke regions of the subject's brain.

In some embodiments, the shape of the stroke region is approximated by overlapping ellipses in a two-dimensional plane, and the spatial dimensions of the stroke region are determined by determining the spatial dimensions of the overlapping ellipses.

In some embodiments, the spatial dimensions of each of the overlapping ellipses are determined as two geometrical parameters.

In some embodiments, the spatial dimensions of the stroke region are determined by determining four geometrical parameters.

In some embodiments, the apparatus includes repeating steps (ii) and (iii) at successive times to monitor growth or shrinkage of the stroke region over time.

The gradient-free optimisation method may be a Nelder-Mead gradient-free optimisation method.

In accordance with some embodiments of the present invention, there is provided at least one computer-readable storage medium having stored thereon instructions that, when executed by at least one processor of a brain monitoring apparatus, cause the at least one processor to execute the steps of any one of the above processes.

BRIEF DESCRIPTION OF THE DRAWINGS

Some embodiments of the present invention are hereinafter described, by way of example only, with reference to the accompanying drawings, wherein:

FIG. 2 shows the different optimization operations of Nelder-Mead ("NM") optimisation represented as geometrical operations in a 3D space of parameters for the three stroke parameters $a_0$, $b_0$, and $\varepsilon_r$ (the geometric parameters $a_0$ and $b_0$ being shown in FIG. 1A);

FIG. 5A shows the effect of the total number of antennas when SNR=15 dB, and FIG. 5B shows the effect of SNR, FIG. 5C shows the effect of stroke size when SNR=15 dB, and FIG. 5D shows the effect of difference between each individual tissue and the database in Gabriel when SNR=15 dB;

FIG. 6: Retrieval process of NM optimization for a 3D MRI-derived stroke mode, wherein:

DETAILED DESCRIPTION

The potential of EMT as a monitoring modality motivated the inventors to develop a new EMT process that is suitable for stroke monitoring during the CRP. Indeed, while some of the intrinsic limitations of EMT described above, namely the diffraction effect and the presence of evanescent waves at UHF and S bands, are unavoidable, the inventors determined that the prohibitively long computational time of prior art EMT processes is due to the numerical formulation of the gradient-based optimizations utilized in every prior art EMT system. As these optimizations find the optimum values of "variables" at every pixel of the resulting images, a high computational time is typically required to find these optimum values. To put it another way, if the spatial distribution and dielectric properties of the stroke region within the brain are unknown, then they are considered as variables whose optimum values must be retrieved at every "pixel" of the image (such as that shown in FIG. 1A). Since having a clinically acceptable spatial resolution requires a relatively high number of pixels (even when considering the limited maximum achievable spatial resolution of EMT), prior art EMT computational processes are prohibitively inefficient for stroke monitoring during the CRP. Moreover, the resulting images calculated by these inefficient processes are insufficiently accurate in any case, as is apparent from FIG. 1D.

Figures 1A, 1D:
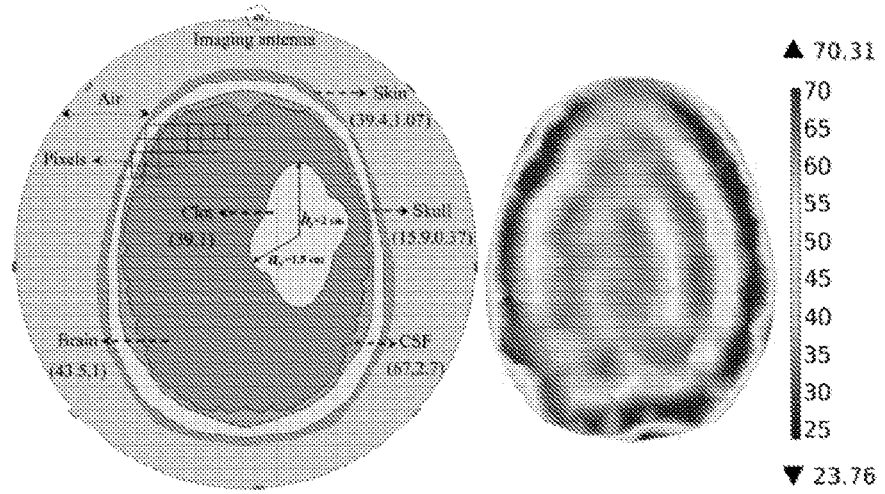
FIG. 1A is derived from a cross-sectional plan view MRI image of a subject's head containing a stroke region, and shows the stroke model information utilized to initiate EMT, with the corresponding tissue dielectric properties ($\varepsilon_r$, $\sigma$) at 1.5 GHz taken from Gabriel.
FIG. 1D is an image of the subject's head generated by a prior art EMT process based on robust gradient-based optimization and without being initiated by the stroke-MRI image, and is clearly not able to accurately identify the stroke region.

With this in mind, the inventors identified that, as the patient is immediately transferred to the imaging unit upon arrival, the initial spatial distribution of the stroke region will be available as a priori information from the early diagnosis stage using a high-resolution imaging modality such as MRI (or X-ray or even EMT), as shown in FIG. 1A, before transferring the patient to the ICU (it takes less than an hour to generate the initial image of the stroke region using the stroke-MRI imaging modality). Although MRI (or X-ray or EMT) imaging cannot practically be used for continuous monitoring for the reasons described above (safety, cost and computational time), the stroke-MRI (or X-ray or EMT) image generated upon patient arrival can be aligned or 'registered' as described in G. Boverman, C. E. L. Davis, S. D. Geimer and P. M. Meaney, *Image registration for microwave tomography of the breast using priors from nonsimultaneous previous magnetic resonance images*, IEEE Journal of Electromagnetics, RF and Microwaves in Medicine and Biology, vol. 2, no. 1, pp. 2-9, March 2018, and in R. L. Leijsen, W. M. Brink, C. A. T. van den Berg, A. G. Webb and R. F. Remis, *Three-dimensional contrast source inversion-electrical properties tomography*, IEEE Trans. Med. Imag., vol. 37, no. 9, September 2018 ("Leijsen"), where the dielectric properties of the different tissues are given in Leijsen.

Figures 1B, 1E:
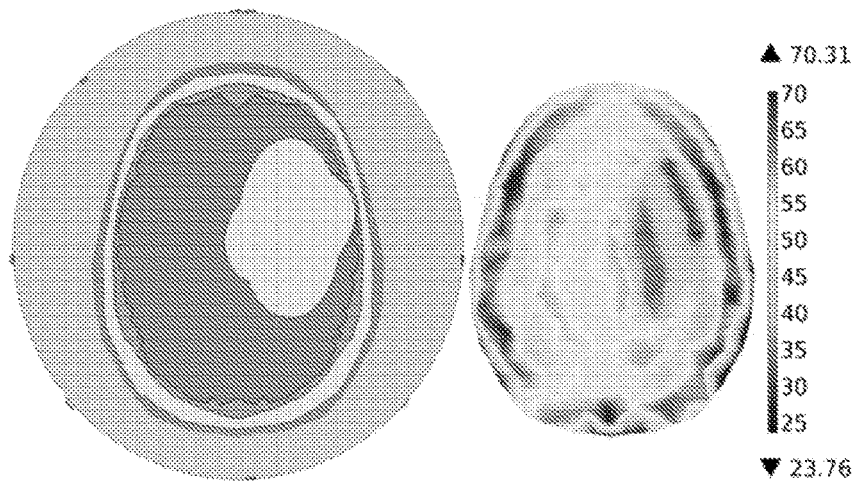
FIGS. 1B and 1C show two corresponding possible critical responses of the stroke of FIG. 1A during CRP as per Schellinger.
FIGS. 1E and 1F are corresponding EMT images generated by the same process as for FIG. 1D, but initiated by the stroke-MRI image of FIG. 1A, FIG. 1E accurately identifying the stroke region, and FIG. 1F showing its subsequent response to medication (thrombolysis) at every pixel. Nevertheless, this improved EMT retrieval process takes more than an hour, making the approach impractical for stroke monitoring during CRP.
Figures 1C, 1F:
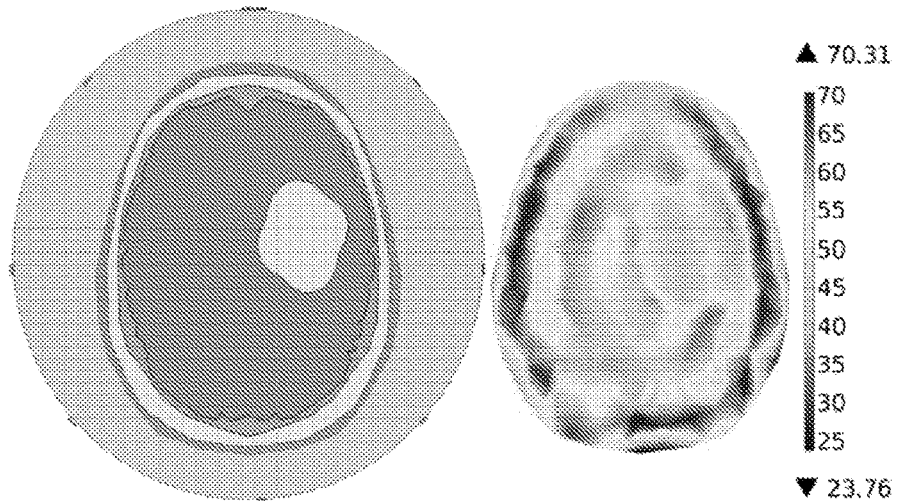

The registered image (of FIG. 1A in this example) can be adopted in an otherwise conventional EMT apparatus installed in the ICU (indeed, the MRI is performed only once), and then used as a priori information to generate images of the stroke responses (shown schematically in FIGS. 1B and 1C), as shown in FIGS. 1E and 1F, demonstrating a significant improvement in retrieval accuracy. The reason for the improvement is that the registered Stroke-MRI image is used to confine the space of possible retrievable images generated by the gradient-based optimizations, leading the EMT to converge to a more accurate image. However, due to the pixel-based optimization nature of conventional (and thus gradient-based) EMT, the computational time of the method is still prohibitively high, around one hour for this example. This is just a slight reduction in time compared to the example of FIG. 1D, where no MRI image supplements the EMT (76 minutes). Therefore, gradient-based EMT might only be useful for non-emergency scenarios such as tumor screening, if initiated by MRI, X-Ray or CT-Scan images (for 3D problems, the reported computational time is around 11 hours on a standard computer, as described in Leijsen).

Described herein are an apparatus and process for continuous monitoring of a brain stroke during a critical rehabilitation period (CRP), also referred to herein for convenience as a stroke monitoring apparatus and process. In the stroke monitoring process and apparatus described herein, the MRI (or X-ray or EMT) registered image is implemented as a priori information to provide the initial geometrical shape and dielectric properties of the stroke region. However, instead of the inefficient prior art gradient-based EMT processes that calculate variables at every pixel of the imaged region, the shape, dimensions, and dielectric properties of the stroke region are calculated as global parameters. Accordingly, the global values of these parameters are continuously updated at later monitoring times by a gradient-free optimization process, as described below.

For example, in the described embodiments the parameters are the two geometrical ones defining the shape and dimensions of the stroke region as the semi-major axes of two overlapping ellipses with fixed minor axes of 1 cm, as shown in FIG. 1A, i.e. $a_0$ and $b_0$ (with initial values of $a_0$=1.5 cm and $b_0$=2 cm), and a third parameter defining the relative permittivity i.e. $\varepsilon_r$ of the stroke region. Treating the shape and dielectric properties of the stroke as global parameters reduces the number of unknown quantities from, say, around 1000 pixel-based variables for the image in FIG. 1A, to only 3 global parameters. This reformulation enables gradient-free optimizations to be used for EMT as highly efficient techniques for parameter-optimization (since parameters are optimized globally, not locally at each pixel). Clearly, such gradient-free optimisations are unable to provide pixel-based images such as those of FIGS. 1D to 1F. However, and regarding the medical needs during CRP, rapid and accurate tracking of stroke parameters (e.g., $a_0$, $b_0$ and $\varepsilon_r$) every two minutes is much more medically relevant than obtaining a coarse image of stroke on an hourly time-basis by gradient-based optimization.

Gradient-free optimization methods were developed to solve problems for which gradient-based optimizations were not applicable, in particular, when the function to be minimized during optimization is not differentiable or smooth.

Various gradient-free optimization methods have been developed for different electromagnetic and antenna applications, including the Nelder-Mead ("NM"), genetic algorithm ("GA"), and particle swarm optimization ("PSO") methods. Where the computational time is the main concern in the optimization procedure apart from accuracy, the NM optimization method is usually the fastest gradient-free optimization method. In the context of stroke monitoring during CRP, where time is life, the inventors consider that NM optimization best suits the monitoring requirements (although other gradient-free optimization method may be used in other embodiments). As NM optimization has not been previously used for EMT applications, an overview of the NM optimization process for this particular application is described below. The general NM methodology is described in N. Pham, A. Malinowski and T. Bartczak, "*Comparative study of derivative free optimization algorithms*," IEEE Trans. Industr. Inform., vol. 7, no. 4, pp. 592-600, November 2011 ("Pham").

Figure 7:
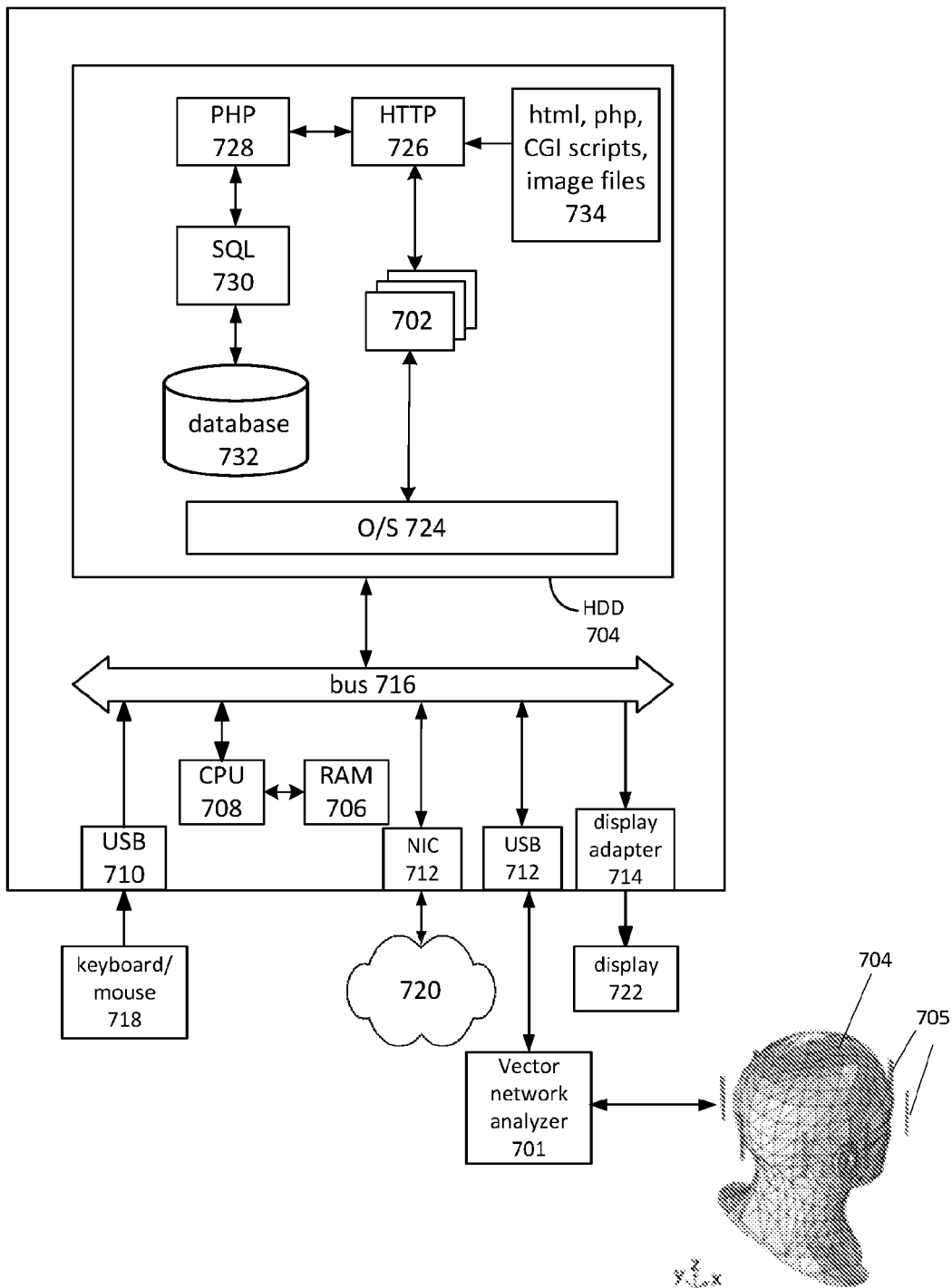
FIG. 7 is a schematic diagram of a stroke monitoring apparatus in accordance with an embodiment of the present invention.
Figure 8:
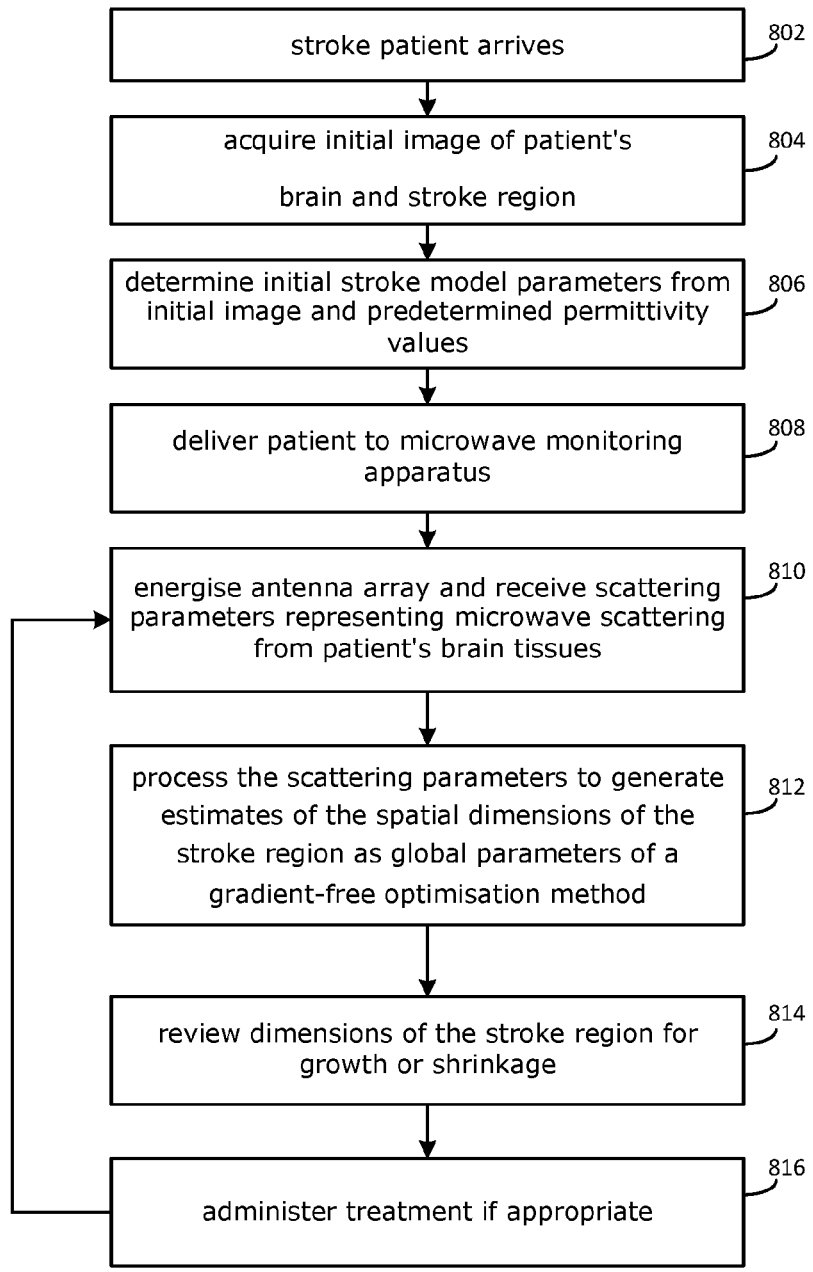
FIG. 8 is a flow diagram of a stroke monitoring process in accordance with an embodiment of the present invention.

In the described embodiments, the described processes are executed by a stroke monitoring apparatus, as shown in FIG. 7. In use, the apparatus is in communication with a vector network analyser (VNA) or transceiver 701 that is in turn connected to an array of microwave antennas 705.

The array of microwave antennas 701 is arranged to receive the head 704 of a patient whose brain is to be imaged, as shown, so that each antenna of the array can be selectively energised to radiate electromagnetic waves or signals of microwave frequency into and through the subject's head to be scattered and the corresponding scattered signals detected by all of the antennas of the array, including the antenna that transmitted the corresponding signal.

As will be apparent to those skilled in the art, the vector network analyser (VNA) 701 energises the antennas as described above, and records the corresponding signals from the antennas as data (referred to herein as 'scattering' data) representing the amplitudes and phases of the scattered microwaves in a form that is known in the art as "scattering parameters" or "S-parameters". The VNA 701 sends this data to the apparatus for processing to generate information on internal features of the imaged object (e.g., brain clots, bleeding sites, and other features). In the described embodiments, a VNA which has a large dynamic range of more than 700 dB and a noise floor below −700 dBm, can be used to activate the antennas to transmit electromagnetic signals across the frequency band of 0.5 to 4 GHz and receive the scattered signals from those antennas.

Although the apparatus of the described embodiments is in the form of a computer, this need not be the case in other embodiments. As shown in FIG. 7, the stroke monitoring apparatus of the described embodiments is a 64-bit Intel Architecture computer system, and the stroke monitoring processes executed by the stroke monitoring apparatus are implemented as programming instructions of one or more software modules 702 stored on non-volatile (e.g., hard disk or solid-state drive) storage 704 associated with the computer system. However, it will be apparent that at least parts of these processes could alternatively be implemented in one or more other forms, for example as configuration data of a field-programmable gate array (FPGA), or as one or more dedicated hardware components, such as application-specific integrated circuits (ASICs), or as any combination of such forms.

The stroke monitoring apparatus includes random access memory (RAM) 706, at least one processor 708, and external interfaces 710, 712, 713, 714, all interconnected by a bus 716. The external interfaces include a network interface connector (NIC) 712 which connects the stroke monitoring apparatus to a communications network such as the Internet 720, and universal serial bus (USB) interfaces 710, at least one of which may be connected to a keyboard 718 and a pointing device such as a mouse 719, and a display adapter 714, which may be connected to a display device such as an LCD panel display 722.

The stroke monitoring apparatus also includes an operating system 724 such as Linux or Microsoft Windows, and in some embodiments includes additional software modules 726 to 730, including web server software 726 such as Apache, available at http://www.apache.org, scripting language support 728 such as PHP, available at http://www.php.net, or Microsoft ASP, and structured query language (SQL) support 730 such as MySQL, available from http://www.mysql.com, which allows data to be stored in and retrieved from an SQL database 732.

Together, the web server 726, scripting language module 728, and SQL module 730 provide the stroke monitoring apparatus with the general ability to allow remote users with standard computing devices equipped with standard web browser software to access the stroke monitoring apparatus and in particular to monitor the progress of a stroke during the CRP.

A. NM Optimization for EMT: Initialization

For the EMT problems shown in FIGS. 1B and 1C (initiated by FIG. 1A), eight imaging dipole antennas are arranged in a circular configuration surrounding the head of a subject so that the 2D MRI model of the subject's head crosses the ports of the dipole antennas (because the S-matrix that is implemented in the optimization process is recorded at the dipole ports).

The antennas illuminate the head with a sinusoidal electromagnetic wave at 1.5 GHz, say five and a half hours after symptoms onset, when thrombolysis has already been applied. This timing example is taken from a stroke case described in Schellinger, where the subject's arrival time is around 3 hours after symptom onset, and the 2D single-slice stroke-MRI is prepared 0.75 hours after arrival. The antennas then record the corresponding scattered fields in the form of an S-matrix (the effects of the number of antennas on the accuracy and retrieval time are discussed below). This S-matrix is then implemented to update the three stroke parameters $a_0$, $b_0$, $\varepsilon_r$ whose initial values in FIG. 1A are $X_0=(a_0=1.5$ cm, $b_0=2$ cm, $\varepsilon_r=39)$, which can be considered to define a point (or vertex as described below) in 3D space (as the number of parameters is 3).

These parameters were selected for the following reasons. Since the effect of any medication applied to a stroke is reflected by the change in the relative permittivity $\varepsilon_r$ of the stroke region of the subject's brain, it can be considered as a reliable parameter to monitor the stroke and converge to a value that matches the S-matrix at later times. As described above, since the retrieval accuracy of the conductivity $\sigma$ of the stroke region is usually poor by comparison with the relative permittivity $\varepsilon_r$, the conductivity is excluded from retrieval. Moreover, the geometrical or shape parameters $a_0$, $b_0$ are chosen to best reflect the geometrical change (extension or shrinkage) of the stroke region. For the smooth stroke shape shown in FIG. 1A, $a_0$, $b_0$ are the semi-major axes of two ellipses that are considered to most accurately represent the geometrical changes of the stroke region with respect to possible alternative geometrical parameters (more complicated geometries are discussed below). The inventors have found that these shape parameters also continuously converge to values that best fit the corresponding S-matrix. The 2D physical problem domain in FIG. 1A is different from the 3D mathematical space of parameters constructed in FIG. 2A.

In addition to $X_0$, the variation range of the three parameters defines the available parameter space, assuming that the stroke region subject to hypoperfusion (FIG. 1B) can be extended across the entire left hemisphere of the brain, and that successful clot breakdown (FIG. 1C) can entirely remove the clot (i.e., shrink the stroke region to nothing). This large variation range corresponds to a parameters space of $0 \leq a_0 \leq 4$ cm, $0 \leq b_0 \leq 7$ cm, and $39 \leq \varepsilon_r \leq 43.5$, indicating that the optimisation process does not require very accurate parameter ranging in finding the optimum vertex, even if there is no solid prediction about the stroke response to medication. To optimize these 3 parameters, the NM optimization first constructs an equal-length simplex (generalized triangle) with 3+1 vertices within the 3D space of parameters, as shown in FIG. 2A. One of the vertices is, indeed, the initial guess (i.e., starting point) $X_0$ provided by the initial MRI image. All other vertices with equal distance c are derived by adding the following vectors to this initial guess, as follows:

$$X_1 = X_0 + (p,q,q)$$

$$X_2 = X_0 + (q,p,q)$$

$$X_3 = X_0 + (q,q,p) \quad (1)$$

where the vector components are, $$q = \frac{c}{N\sqrt{2}}(\sqrt{N+1} - 1) \quad (2)$$

$$p = q + \frac{c}{\sqrt{2}}$$

and where N is the number of parameters (i.e., 3 in the described embodiments). Typically, c=1 to allow the process to search in a sufficiently large volume at the initial step. Small values for c normally require a long computational time and can mislead the process to find only a local minimum. Moreover, as the presence of noise can cause slightly different vertices to result in the same frequency response (S-matrix), locating the vertices far enough from one another (distanced with c≥1) makes the process robust with respect to noise at early iterations.

By constructing the simplex, the next step is to evaluate an objective function (i.e., the function to be minimized by the NM optimization) at every vertex $X_0$, $X_1$, $X_2$, $X_3$. In the EMT problem of FIG. 1B or 1C, this objective function is defined as the $L_2$ norm mismatch between the measured ("meas.") S-matrix and the retrieved ("retr.") S-matrix, as follows:

$$F(a_0, b_0, \varepsilon_r) = \|S^{meas.} - S^{retr.}\|^2 = \quad (3)$$
$$\left\| S^{meas.} - k_0^2 \int_\Omega G(a_0, b_0, \varepsilon_r) \cdot (\chi(a_0, b_0, \varepsilon_r) E(a_0, b_0, \varepsilon_r)) d\Omega \right\|^2$$

where $\Omega$ denotes the imaged domain (in cylindrical coordinates $\hat{a}_\rho$, $\hat{a}_\varphi$, $\hat{a}_z$), $\chi$ is the contrast in the dielectric properties of the human head defined as $$\chi = \left(\frac{\varepsilon}{\varepsilon_0} - 1\right)$$

where $$\varepsilon = \varepsilon_0 \varepsilon_r - j\frac{\sigma}{\omega}$$

is the complex permittivity, $$\varepsilon_0 = \frac{1}{36\pi} \times 10^{-9}$$

is the free-space permittivity, and $\omega = 2\pi \times 1.5$ GHz is the angular frequency, respectively. In the described example with eight antennas, the size of the S-matrix is therefore 8×8;

the mismatch is thus the difference between the corresponding matrix elements of $S^{meas.}$ and $S^{retr.}$. E is the total electric field across the imaged domain of FIG. 1B or 1C, derived as described in Chapter 9 of W. C. Chew, *Waves and Fields in Inhomogeneous Media*, IEEE Press, New York, 1995 ("Chew") and A. Afsari, A. Abbosh, and Y. Rahmat-Samii, "*Modified Born iterative method in medical electromagnetic tomography using magnetic field fluctuation contrast source operator*," IEEE Trans. Microw. Theory Techn., DOI: 10.1109/TMTT.2018.2876228, and given by:

$$E(a_0, b_0, \varepsilon_r) = E^{inc} - k_0^2 \int_\Omega G(a_0, b_0, \varepsilon_r) \cdot (\chi E(a_0, b_0, \varepsilon_r)) d\Omega \quad (4)$$

where $E^{inc}$ is the incident electric field in absence of any object in $\Omega$. Finally, G is the dyadic Green's function given in Chapter 1 of Chew, and $k_0 = \omega\sqrt{\mu_0 \varepsilon_0}$ is the free-space wavenumber, wherein $\mu_0 = 4\pi \times 10^{-7}$ is the free-space permeability.

After evaluating the objective function for all of the vertices, three of the vertices possess special importance in the NM technique, as shown in FIG. 2B. The vertex which gives the smallest value of the objective function (given by Equation (3) in the described embodiments) is referred to as the "best" vertex, and is denoted as $X_b$. The vertex with highest $L_2$ norm mismatch is referred to as the "worst" vertex, $X_w$. In order to guide the process into a direction that always reduces the mismatch in Equation (3), the process determines an auxiliary point for which Equation (3) has the second highest value. This vertex is referred to as the "second worst" vertex, $X_{sw}$. The average value of all of the vertices except $X_w$, is then calculated as $X_a$. The line segment between $X_a$ and $X_w$ ($L_{X_w X_a}$) is always downward, and contains some useful points wherein Equation (3) may have a lower mismatch than $X_w$ during the optimization processes. As per this downward-direction search for the optimum point, the process is also referred to as the "downhill" optimization.

After the above initialization, the process performs at least two, and at most five "error-reduction" operations. In each of these steps, the old value of $x_w$ is removed from the computer memory (i.e., is not stored for the next iteration), and all the other vertices are rearranged to provide new values for $x_b, x_w, x_{sw}$. Hereafter, the following operations are introduced:

Reflection: The first optimization step in the NM approach is to reflect the worst vertex x across L, with the same length, as follows:

$$X_r = 2X_a - X_w \quad (5)$$

as shown in FIG. 2c. This operation is to check whether moving in the $L_{X_w X_a}$ direction should be continued by the process or another direction will lead the process to the optimum vertex. If Equation (3) has a lower mismatch at $X_r$ with respect to $X_b$, that is $F(X_r) < F(X_b)$, before replacing $$X_b \leftarrow X_r$$

$$X \leftarrow X_b$$

$$X_{sw} \leftarrow X$$

$$X_w \leftarrow X_{sw} \quad (6)$$

the process evaluates the chance of finding even a better vertex (where the programming convention A←B represents that the old value A is substituted by the new value B). To this end, the expansion operation is always performed by further moving in the same direction $L_{X_r X_a}$.

Expansion: As per FIG. 2d, the process further moves along $L_{X_w X_a}$ with the same step-length i.e.

$$X_e = 2X_r - X_a \quad (7)$$

Then, Equation (3) is also evaluated at this expansion vertex. If its value is lower than $X_b$ (even if it is worse than $X_r$) i.e. $F(X_e) < F(X_b)$, the process replaces $$X_b \leftarrow X_e$$

$$X \leftarrow X_b$$

$$X_{sw} \leftarrow X$$

$$X_w \leftarrow X_{sw} \quad (8)$$

and (iteratively) returns to the reflection step. The reason that the process does not immediately accept $X_b \leftarrow X_r$, despite it being the best-found vertex among the other vertices, comes from the fact that this vertex is reserved by the process, as it lies inside the new simplex formed by $X_e$. Hence, by performing the expansion, the neighborhood domain of $X_r$ is merely safeguarded as the subdomain wherein some other good or even better vertices may exist to minimize Equation (3). Nevertheless, if Equation (3) at $X_e$ is not lower than $X_b$, then the substitutions of Equation (6) are performed and the process iteratively returns to the first operation (i.e., reflection).

Forward Contraction: Either Equation (6) or Equation (8) assumes $F(X_r) < F(X_b)$. If this is not realized, but $F(X_{sw}) < F(X_r) < F(X_w)$, the process has excessively moved along the $L_{X_w X_a}$ direction, and better vertices may lie at distances closer than $X_r$. Accordingly, the forward contraction along $L_{X_r X_a}$ is performed by returning back half a step-length (typically the balanced step-length) from $X_r$ toward $X_a$ as shown in FIG. 2E, i.e.

$$X_{fc} = 1.5X_a - 0.5X_w \quad (9)$$

If $F(X_{fc}) < F(X_r)$, a new simplex is formed on vertices X, $X_b$, $X_{sw}$, $X_{fc}$ by returning to the initialization step and rearranging these vertices from the worst to the best one.

Backward Contraction: If $F(X_w) < F(X_r)$, then $L_{X_w X_a}$ may still contain some vertices that can improve the mismatch in Equation (3), and in the same way as forward contraction, a backward contraction is performed by moving backward half a step-size from $X_a$ toward $X_w$, as shown in FIG. 2f, as follows:

$$X_{bc} = 0.5X_a + 0.5X_w \quad (10)$$

If $F(X_{bc}) < F(X_w)$, then a new simplex as shown in FIG. 2f is constructed on X, $X_b$, $X_{sw}$, $X_{bc}$ by returning to the initialization step and rearranging the vertices from the worst to the best.

Shrinking: If, nonetheless, none of the above conditions takes place, then the last step to find a better direction toward the optimum vertex is to shrink the simplex. To this end, only the best vertex $X_b$ is kept, and for the other vertices, the shrinking operation is performed as follows (for each ith vertex):

$$X_i(new) = 0.5X_b + 0.5X_i(old) \quad (11)$$

Then, the process returns to the initialization step to rearrange the new vertices formed in the shrinking step shown in FIG. 2g. This iterative process of NM optimization is continued until $F(X_b)$ meets the truncation condition of the objective function, in the described embodiment being:

$$F(X_b) < 10^{-7} \quad (12)$$

Figure 3:
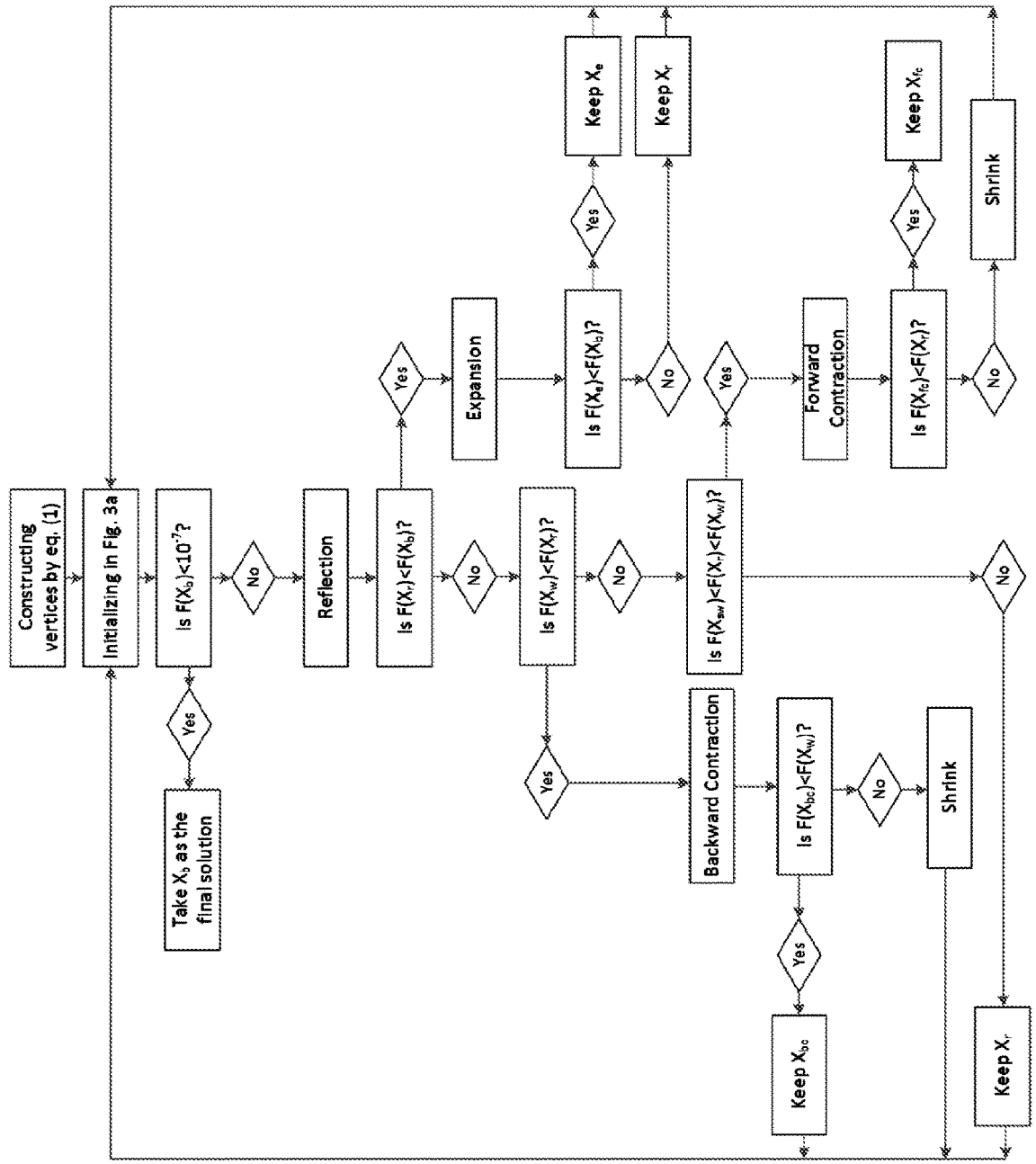
FIG. 3 is a flowchart of an NM optimization process in accordance with the described embodiments of the present invention; after constructing the vertices, the process firstly checks whether the "best" vertex satisfies the truncation condition or not. If not, the first error reduction operation i.e. "reflection", is performed. Accordingly, if the reflection vertex has a lower error with respect to the best vertex, then the expansion operation is performed with the hope of finding an even better vertex. If not, depending on the error level of the reflection vertex with respect to the worst and second worst vertices, forward/backward contractions and shrinking are performed to finally find a new vertex that is, at minimum, better (has a lower error) than the "worst" vertex in each iteration.

The value of $X_b$ that satisfies the truncation condition is stored as the final result. The truncation condition in Equation (12) is chosen to be very small, so as to ensure that the required accuracy in retrieving the parameters is satisfied. Larger values of truncation conditions do not lead to very accurate parameter retrieval. To demonstrate all these steps at once, FIG. 3 is a flowchart of the NM optimization process for EMT, and corresponding pseudocode is given below.

| Steps | Commands |
|---|---|
| 1: | Input: introduce parameters $a_0$, $b_0$, $\varepsilon_r$ |
|  | Input: parameters' range $0 \leq a_0 \leq 4$ cm, $0 \leq b_0 \leq 7$ cm, $39 \leq \varepsilon_r \leq 43.5$ |
|  | Input: $X_0$ |
|  | Input: Measured S-parameters of Fig. 1B or 1C |
| 2: | Do: vertex construction: eq. (1) |
|  | Do: vertex rearrangement: Fig. 3A |
|  | Do: calculation of $X_a$ |
| 3: | if (12) is satisfied |
|  |     Output: $X_b$ |
|  | else |
|  |     Do Reflection |
|  |     if $F(X_r) < F(X_b)$ |
|  |         Do Expansion |
|  |         if $F(X_e) < F(X_b)$ |
|  |             Perform (8) by returning to Vertex Rearrangement |
|  |         else |
|  |             Perform (6) by returning to Vertex Rearrangement |
|  |         end |
|  |     else if $F(X_w) < F(X_r)$ |
|  |         Do Backward Contraction |
|  |         if $F(X_{bc}) < F(X_w)$ |
|  |             Accept $X_{bc}$ and Return to Vertex Rearrangement |
|  |         else |
|  |             Shrink and Return to Vertex Rearrangement |
|  |         end |
|  |     else if $F(X_{sw}) < F(X_r) < F(X_w)$ |
|  |         Do Forward Contraction |
|  |         if $F(X_{fc}) < F(X_r)$ |
|  |             Accept $X_{fc}$ and Return to Vertex Rearrangement |
|  |         else |
|  |             Shrink and Return to Vertex Rearrangement |
|  |         end |
|  |     else |
|  |         Accept $X_r$ and Return to Vertex Rearrangement |
|  |     end |
|  |     end |
|  |     end |
|  | end |

I. NM Gradient-Free Optimization in Practice: 2D Retrieval

To efficiently monitor the different stroke behaviours known as hypoperfusion and shown in FIG. 1B or the clot-breakdown in FIG. 1C, the NM optimization process described above is utilized to optimize the three parameters $a_0$, $b_0$, and $\varepsilon_r$. The reason for merely choosing the shape parameters $a_0$ and $b_0$ for optimization and excluding location parameters such as the coordinate of the center of the stroke in FIG. 1B or 1C comes from the fact that in either hypoperfusion or clot-breakdown process, the stroke location does not change. Instead, the stroke merely extends or shrinks around its center.

A. NM Optimization Performance

Figure 4A:
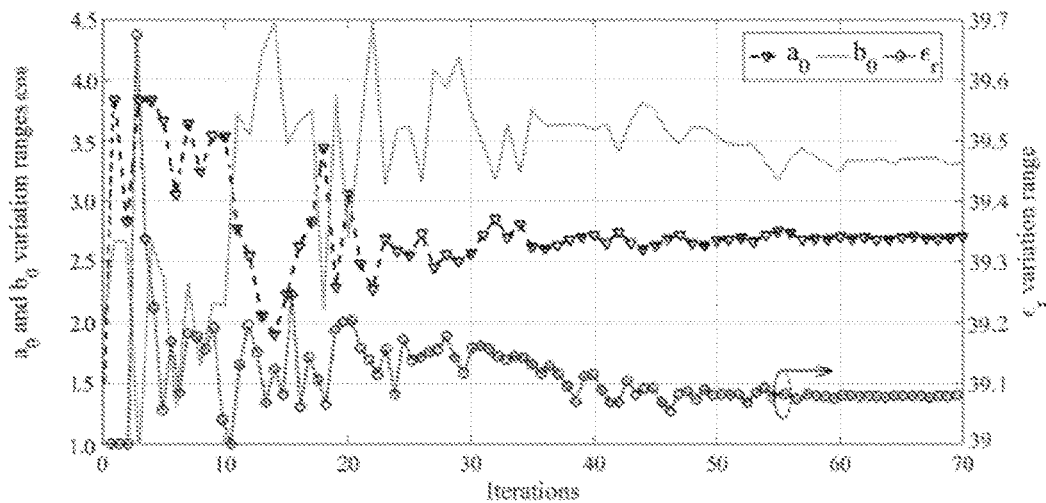
FIGS. 4A to 4C are respective graphs representing the retrieval process and convergence behavior of the NM optimization process described herein.

For hypoperfusion, the actual values of the parameters in the given example are $a_0=2.5$ cm, $b_0=3$ cm, $\varepsilon_r=39$, and the retrieved ones, whose evolution over successive iterations are shown in FIG. 4A, are $a_0=2.68$ cm, $b_0=3.32$ cm, $\varepsilon_r=39.08$. As FIG. 5A shows, the NM process variations gradually become stable when the simplex becomes smaller during iterations. For the clot-breakdown of FIG. 1C, the actual and retrieved values of the NM optimization process are $a_0=1$ cm, $b_0=1$ cm, $\varepsilon_r=40$, and $a_0=0.997$ cm, $b_0=1.002$ cm, $\varepsilon_r=40.07$ (FIG. 4B), respectively. It is to be noted that the relative permittivity of the affected area, during clot-breakdown, is again approaching that of the brain, when being recovered. In both cases, although the simulation environment is highly noisy (the SNR of the S-matrix is set to 15 dB), the parameters are nevertheless accurately updated. To provide a quantitative analysis of this accuracy, a "retrieval error" is defined as:

$$10\log\left(\frac{\left|\sum_{i=1}^{3}(\text{parameter}_i^{actual} - \text{parameter}_i^{retrieved})\right|}{\left|\sum_{i=1}^{3}\text{parameter}_i^{actual}\right|}\right) \quad (13)$$

The retrieval error is low in each case: −18.86 dB for the hypoperfusion outcome, and −27.95 dB for the clot-breakdown outcome.

The critical point, however, is the retrieval time. As per FIG. 4C, the process terminates once the termination condition of Equation (12) is satisfied. In the described examples, the hypoperfusion and clot-breakdown retrievals require 94 and 69 iterations, respectively, and each iteration takes 1.25 seconds. Hence, within every two minute timeframe, the stroke is continuously monitored to evaluate the treatment process and make instant preparations for craniotomy if required (the surgical removal of a part of the subject's skull to directly access the affected area).

Figure 4B:
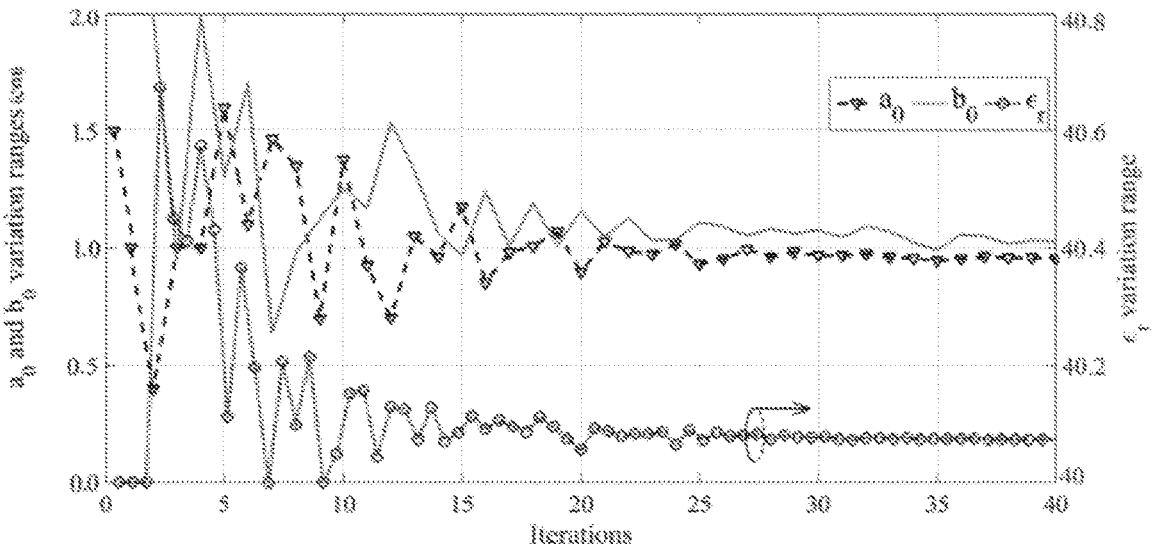
Figure 4C:
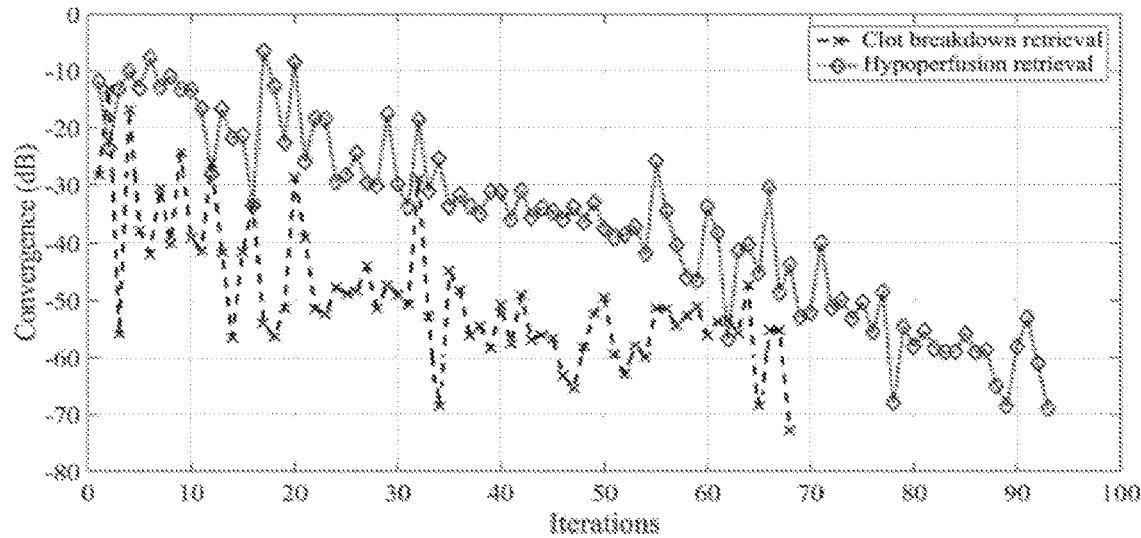
Figure 5A:
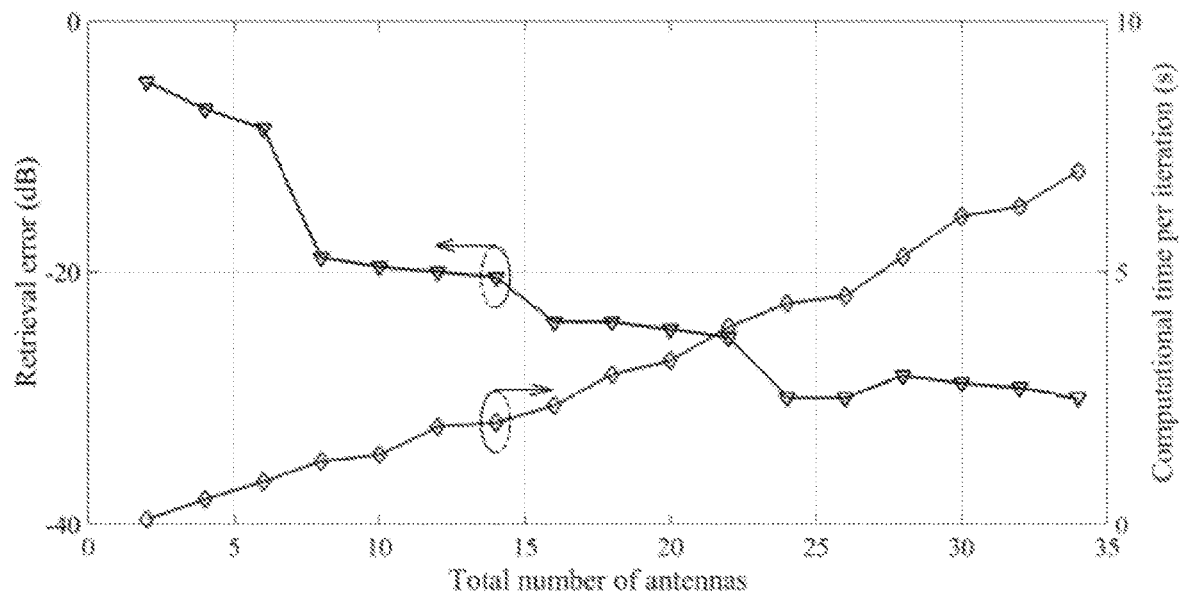
FIGS. 5A to 5D are respective graphs showing the effects of some influential factors on the accuracy and computational time of NM optimization in stroke monitoring during the CRP with 8 antennas, and using the two stroke shape parameters $a_0$, $b_0$.

FIGS. 4A and 4B provide a graphical illustration of the performance of the NM process respectively over the first 70 and 40 iterations only (the variations of the retrieved parameters in further iterations being too small to be usefully plotted in the same graph). The greater geometrical change caused by hypoperfusion with respect to the initial topology (i.e. FIG. 1A) in comparison with the clot-breakdown process results in a higher retrieval error and a longer convergence time when compared to the clot-breakdown retrieval.

A. Influential Factors on Accuracy and Computational Time

Among the different factors affecting the accuracy (retrieval error) and computational time of EMT based on NM optimization, the major contributors are: the total number of imaging antennas, the SNR, the shape parameters $a_0$, $b_0$, and the minor difference in the dielectric properties of each subject's head tissues with respect to the database described in C. Gabriel, S. Gabriel and E. Corthout, "*The dielectric properties of biological tissues: I. Literature survey*", Phys. Med. Biol., vol. 41, no. 1, pp. 2231-2249, 1996 ("Gabriel") utilized to register the initial stroke-MRI image. To depict these influences, as the retrieval of hypoperfusion is more challenging (having a higher retrieval error), the effects of the number of antennas, SNR, and the accuracy level of Gabriel are described for this medical scenario.

FIG. 5A shows that increasing the number of antennas up to a specific level remarkably improves the accuracy at the expense of increasing the computation time per iteration. This improvement comes from the fact that having additional antennas is equal to having more information. For the same reason, the total number of iterations reduces from 94 to 78, as the space of possible solutions is now more confined, and the process requires fewer iterations to satisfy the truncation condition. Nevertheless, due to the increase in the size of the objective function, whose size corresponds to the size of the S-matrix, the computational time per iteration drastically increases. Indeed, having M imaging antennas results in an M×M S-matrix. In the literature, 8 has been suggested as the minimum number of antennas to provide a medical image of the head with acceptable accuracy.

Figure 5B:
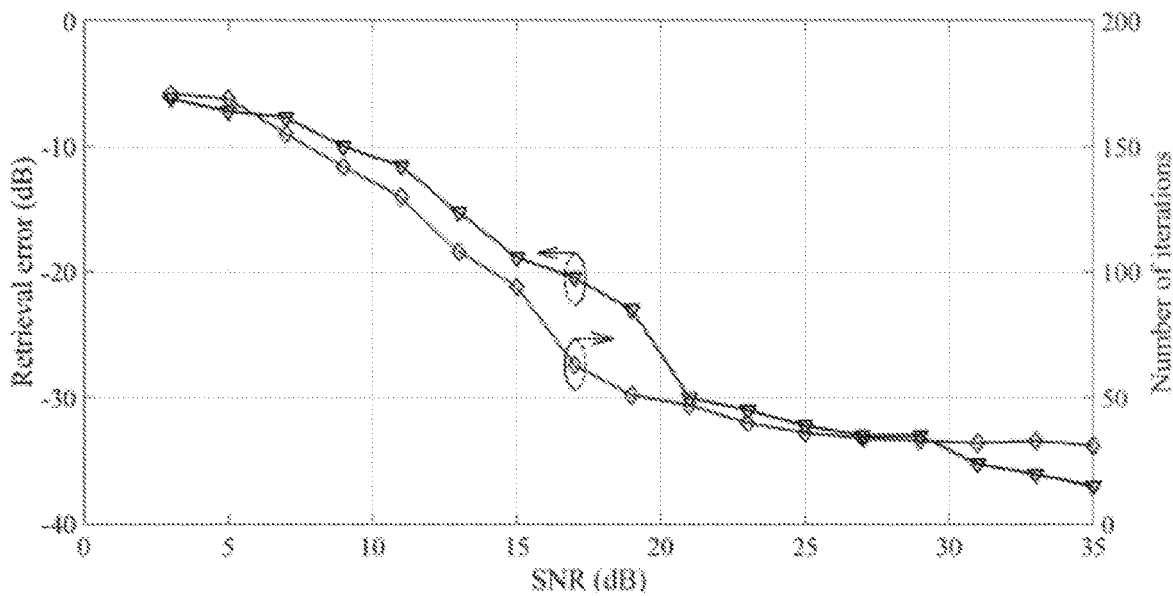

The second factor to consider is the SNR. When the measured data are highly contaminated by noise, the vertices that are close to each other (having close parameter values in FIG. 2A) possess very similar frequency responses that are most likely dominated by noise. Thus, the accuracy of the process is degraded as it is no longer able to discriminate between close vertices. If the medical imaged domain is highly isolated with respect to noise, both the retrieval accuracy and the required number of iterations are improved as shown in FIG. 5B. This is because the measured S-matrix in Equation (3) contains more reliable information to retrieve the stroke response (hypoperfusion), and thus, the vertex that best minimizes the objective function in Equation (3) is closer to the actual one. The computational time per iteration remains unchanged i.e. 1.25 seconds, as this time is a function of the number of imaging antennas and the retrieval parameters.

Figure 5C:
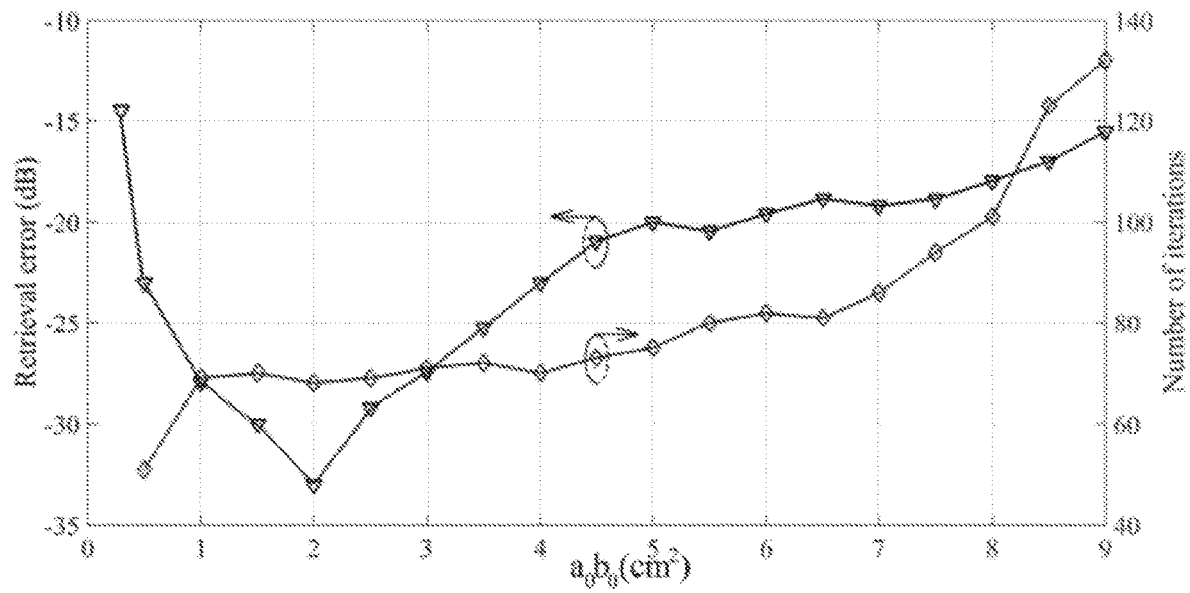

The next factor to consider is the size-range of the stroke region that can be retrieved accurately. To this end, the cross-sectional factor $a_0 \times b_0$, as a rule of thumb, is introduced to represent the stroke size. FIG. 5c shows that the retrieval process becomes inaccurate for the example in FIG. 1B if $a_0 \times b_0 < 0.64$ cm² or $a_0 \times b_0 > 9$ cm². As described above, the diffraction effect and the presence of evanescent waves are noticeable in the UHF and S bands, and these effects become highly destructive when the size of the stroke region becomes less than a quarter-wavelength. As the wavelength at 1.5 GHz is 3.2 cm inside the clot (with $\varepsilon_r = 39$), the quarter-wavelength is 0.8 cm, resulting in 0.64 cm² cross-sectional factor, below which the retrieval accuracy decreases substantially. On the other hand, for a very high cross-sectional factor e.g., $a_0 \times b_0 > 9$ cm², the change in the stroke shape is not accurately trackable as this change unavoidably requires additional shape parameters (besides $a_0$, $b_0$) to more accurately model the irregularity and asymmetry of the stroke, especially when the stroke is deformed by the skull from one side, but is still extendable from the other side. From the computational time perspective, if only two shape parameters are employed for large-size stroke regions, the process requires more iterations with respect to the stroke in FIG. 1B to partially conform the initial shape of the stroke to the extended one, as shown in FIG. 5c. This results from the fact that adding each shape parameter with its corresponding variation range will more confine the space of possible solutions. Dealing with only two shape parameters does require more iterations to partially match the irregularity and asymmetry of extended stroke (this is demonstrated below). Nevertheless, it is noted that increasing the number of stroke parameters, as a solution to improve the retrieval error and reduce the total iterations, does not necessarily reduce the computational time, as adding each parameter to the problem adds another dimension to the space of parameters. Accordingly, the computational time per iteration increases exponentially.

Figure 5D:
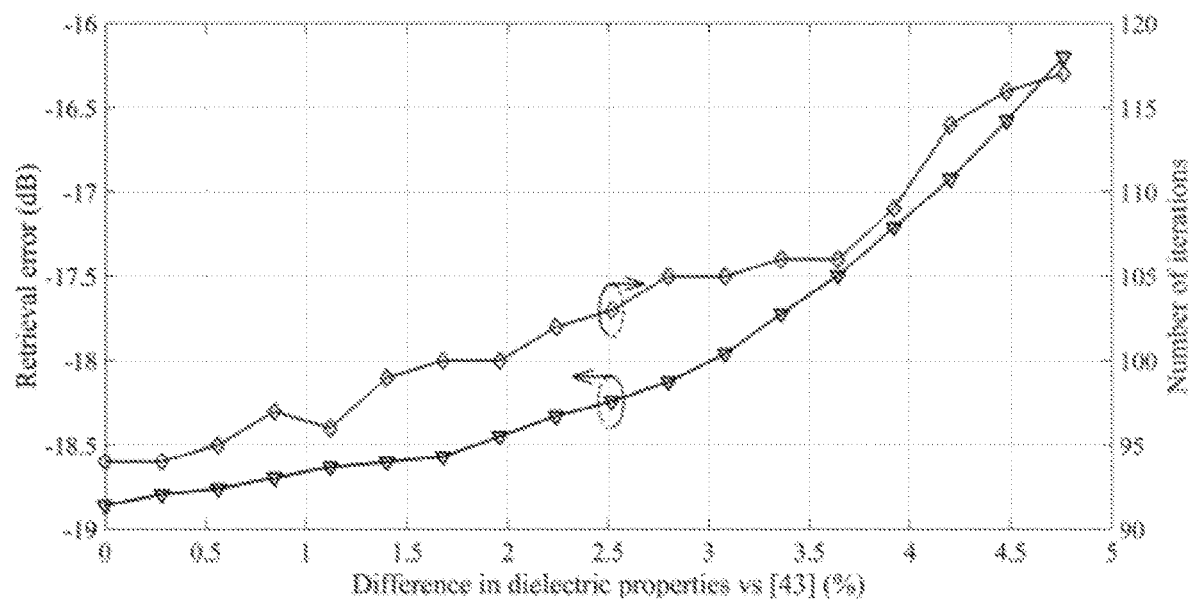

The last factor is the effect of the level of agreement between the database in Gabriel and the dielectric properties of each individual human head. As the gradient-free optimization process merely focuses on retrieving the global stroke parameters, it is very important to ensure that the dielectric properties in Gabriel by which the stroke-MRI is registered into the EMT apparatus are highly accurate to avoid a noticeable retrieval deviation from the desired values. Fortunately, this agreement is typically very high, as the materials constructing the tissues in FIG. 1A are the same for different individuals, and the minor difference between these materials and the database in Gabriel mainly comes from the partial statistical randomness. To take this factor into consideration, FIG. 5d applies up to 5% randomdifference to each tissue in FIG. 1A with respect to their corresponding values reported in Gabriel, to demonstrate the robustness of the process with respect to minor differences in dielectric properties of different head tissues. As seen, both the computational speed and retrieval error slightly drop, while still falling within the acceptable requirements of the CRP.

By studying the effects of influential factors on the accuracy and computational time of the NM optimization process in medical EMT application, the process is applied below to a more complicated problem where a 3D MRI-derived stroke model, as per FIG. 4 of Leijsen, supplements the NM process as shown in FIG. 6. Four shape parameters are implemented in 3D to monitor the more complicated clot breakdown process.

I. NM Gradient-Free Optimization in Practice: 3D Retrieval

Figure 6A:
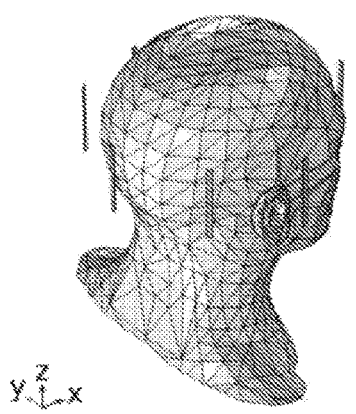
FIG. 6A is a representation of the three-dimensional EMT geometry with a circular array of antennas disposed around the patient's head.
Figure 6B:
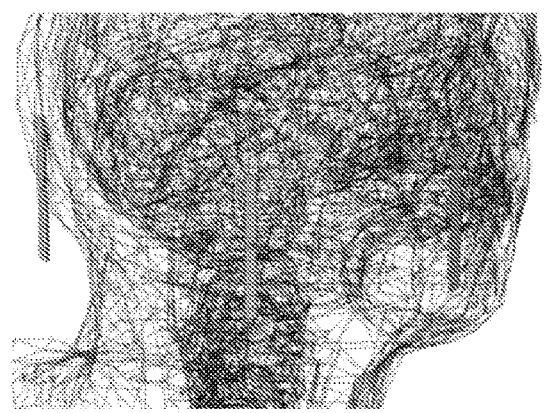
FIG. 6B shows a close up view of a stroke region within the patient's head as imaged by the three-dimensional EMT process described herein.
Figure 6C:
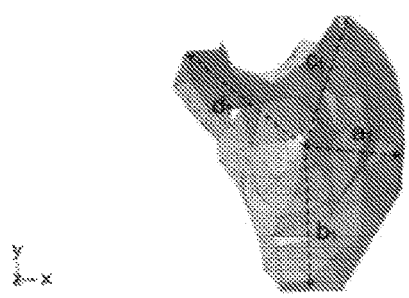
FIG. 6C shows the imaged stroke region with four geometrical parameters that define the three-dimensional stroke region.

For realistic 3D EMT problems, the accuracy of the retrieved parameters can be further improved if either the total electric field within the domain, or the retrieved S-matrix, is simulated using a well-developed numerical method such as finite element modelling (FEM). This can be realized by directly solving the wave equation and considering the entire three-dimensional physical structure of the imaging antennas (see FIG. 6A), rather than using the point-source-based Equations (3) and (4) given above. Indeed, the reason for implementing the point-source-based objective function of Equation (3) given above is that the same objective function is used in prior art gradient-based optimization methods in EMT. Therefore, such a point-source approximation provides a better basis for comparing the two methodologies. Nevertheless, due to the additional complexity of the realistic antenna structures of the problem shown in FIG. 6, the commercial COMSOL software package is used for the simulations. The stroke region within an entire head model is determined as a complex shape defined by triangular mesh elements, as shown in FIG. 6B, and the stroke parameters are illustrated in FIG. 6C with initial values $X'_0=(a_1=0.41$ cm, $b_1=0.4$ cm, $c_1=0.41$ cm, $d_1=0.42$ cm, $\varepsilon_r=39$), these values being the distances from the central point of the stroke region to the four furthest points on the perimeter of the region.

Figure 6D:
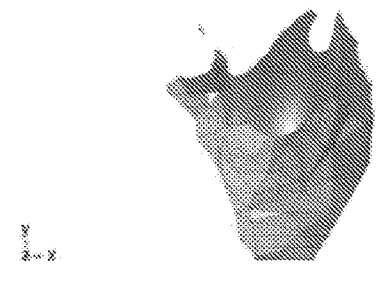
FIG. 6D shows the imaged three-dimensional stroke region during clot breakdown.

When thrombolytic treatment is performed in time, the clot breakdown process starts as seen in FIG. 6d. This process, slightly or significantly, changes the stroke parameters to $X_1=(a_1=0.4$ cm, $b_1=0.395$ cm, $c_1=0.39$ cm, $d_1=0.41$ cm, $\varepsilon_r=42$).

Figure 6E:
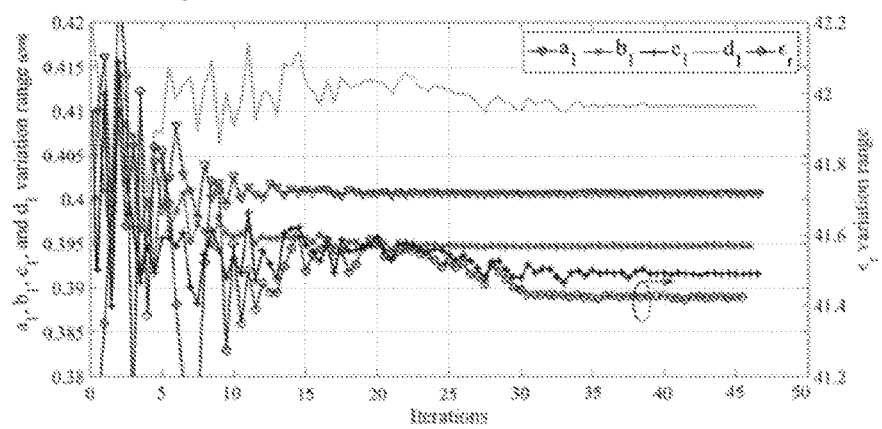
FIG. 6E is a graph of the four geometrical stroke region parameters and the relative permittivity determined by the process as a function of iteration number.
Figure 6F:
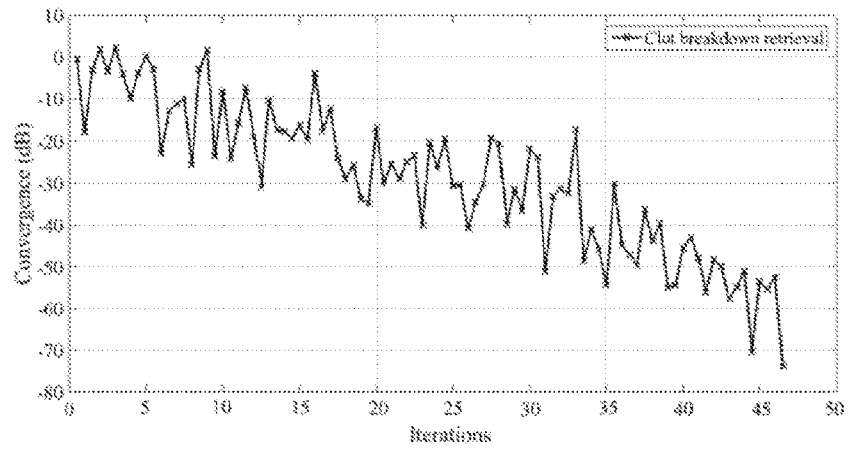
FIG. 6F is a graph showing convergence of the process in dB as a function of iteration number.

As per the graph of FIG. 6E, the retrieved stroke region shape parameters are $X_1=(a_1=0.401$ cm, $b_1=0.395$ cm, $c_1=0.392$ cm, $d_1=0.411$ cm) and the retrieved permittivity of the stroke region is $\varepsilon_r=41.43$, in excellent agreement with their actual values. As FIG. 6D shows, the changes in the spatial dimensions of the stroke region due to clot breakdown are greatest for the shape parameters $c_1$, $d_1$, which is why they require additional iterations to approach their actual values. FIG. 6F is a convergence plot of the NM optimization process. Due to having sufficient shape parameters, fewer than 50 iterations are required to reach the truncation condition. In COMSOL Multiphysics installed on the same PC, due to the large size of the 3D problem domain, each iteration requires 15 seconds to complete. In total, the behaviour of the stroke can be monitored every 11 minutes (i.e., the described apparatus can generate a new group of plots like FIG. 6E every 11 minutes), which is a reasonable time for 3D monitoring during the CRP. Taking the results described in Pham as the ground truth, at least 10 times more computational time is required when the GA or PSO gradient-free methods are used instead of the NM method, e.g. about 110 minutes for this specific problem. This time approaches that of prior art gradient-based optimization methods, and normally exceeds the CRP timeframe. Therefore, the inventors consider that, among the gradient-free methods and general-purpose computer hardware available at the time of writing, only EMT systems based on the NM gradient-free optimizations can be efficiently utilized as 2D or 3D stroke monitoring tools during the CRP.

The EMT monitoring process and apparatus described herein and based on Nelder-Mead gradient-free optimization provide the ability to monitor the expansion or contraction of stroke during the CRP, and can therefore potentially be considered as a translational medical advance to increase the chance of survival from stroke. The results described herein demonstrate that the process is highly efficient to retrieve a 2D stroke response within every 2 minutes, or a 3D stroke response within every 11 minutes on a general-purpose computer platform, while other gradient-free approaches such as GA or PSO can generate the same outputs but at the expense of much longer computational times. The described process can be initiated by stroke-MRI data available from early diagnosis. Then, the shape and dielectric properties (the real part of permittivity) of the stroke region are defined as global parameters. Following this, the patient can be successively imaged by a portable EMT system as described herein using a small number of imaging antennas, and the S-matrix recorded by these antennas at each imaging step is utilized to update the global parameters and thus identify the expansion or contraction of the stroke region, in particular in response to one or more treatments. The described process and apparatus can thus improve the treatment process, and consequently, the chance of survival for victims of stroke.

Many modifications will be apparent to those skilled in the art without departing from the scope of the present invention.

The invention claimed is:

1. A computer-implemented process for continuous monitoring of a brain stroke during a critical rehabilitation period, the process including the steps of:
   (i) accessing initial image data representing an initial image of a subject's brain containing a stroke region;
   (ii) accessing scattering parameter data representing microwaves scattered by the subject's brain and originating from a plurality of antennas disposed around the subject's brain; and
   (iii) processing the scattering parameter data and the initial image data using a gradient-free optimisation method to generate estimates of spatial dimensions of the stroke region within the subject's brain, wherein the initial image of the subject's brain is used as a priori information to improve the accuracy of the generated estimates, and the spatial dimensions of the stroke region are generated as global parameters of the gradient-free optimisation method.

2. The process of claim 1, wherein the spatial dimensions of the stroke region are initially determined by optimising the spatial dimensions of a first predetermined permittivity value of the stroke region and a second predetermined permittivity value for non-stroke regions of the subject's brain.

3. The process of claim 1, wherein the shape of the stroke region is approximated by overlapping ellipses in a two-dimensional plane, and the spatial dimensions of the stroke region are determined by determining the spatial dimensions of the overlapping ellipses.

4. The process of claim 3, wherein the overlapping ellipses have minor axes with fixed spatial dimensions, and the spatial dimensions of the overlapping ellipses are determined as two parameters corresponding to major axes of the overlapping ellipses.

5. The process of claim 1, wherein the spatial dimensions of the stroke region are determined by determining four geometrical parameters.

6. The process of claim 1, including repeating steps (ii) and (iii) at successive times to monitor growth or shrinkage of the stroke region over time.

7. The process of claim 1, wherein the gradient-free optimisation method is a Nelder-Mead gradient-free optimisation method.

8. The process of claim 1, wherein the spatial dimensions and relative permittivity of the stroke region are generated as global parameters of the gradient-free optimisation method.

9. The process of claim 1, wherein the initial image of the subject's brain is generated by magnetic resonance imaging or x-ray imaging or electromagnetic tomography imaging.

10. An apparatus for continuous monitoring of a brain stroke during a critical rehabilitation period, the apparatus including: a memory; at least one processor; and at least one non-transitory computer-readable storage medium having stored thereon instructions that, when executed by the at least one processor, cause the at least one processor to execute the steps of: (i) accessing initial image data representing an initial image of a subject's brain containing a stroke region; (ii) accessing scattering parameter data representing microwaves scattered by the subject's brain and originating from a plurality of antennas disposed around the subject's brain; and (iii) processing the scattering parameter data and the initial image data to estimate spatial dimensions of the stroke region within the subject's brain, wherein the initial image of the subject's brain is used as a priori information to improve the accuracy of the determination, and the spatial dimensions of the stroke region are determined as global parameters of a gradient-free optimisation method.

11. The apparatus of claim 10, wherein the spatial dimensions of the stroke region are initially determined by optimising the spatial dimensions of a first predetermined permittivity value of the stroke region and a second predetermined permittivity value for non-stroke regions of the subject's brain.

12. The apparatus of claim 10, wherein the shape of the stroke region is approximated by overlapping ellipses in a two-dimensional plane, and the spatial dimensions of the stroke region are determined by determining the spatial dimensions of the overlapping ellipses.

13. The apparatus of claim 12, wherein the spatial dimensions of each of the overlapping ellipses are determined as two geometrical parameters.

14. The apparatus of claim 10, wherein the spatial dimensions of the stroke region are determined by determining four geometrical parameters.

15. The apparatus of claim 10, including repeating steps (ii) and (iii) at successive times to monitor growth or shrinkage of the stroke region over time.

16. The apparatus of claim 10, wherein the gradient-free optimisation method is a Nelder-Mead gradient-free optimisation method.

17. The apparatus of claim 10, wherein the spatial dimensions and relative permittivity of the stroke region are generated as global parameters of the gradient-free optimisation method.

18. The apparatus of claim 10, wherein the initial image of the subject's brain is generated by magnetic resonance imaging or x-ray imaging or electromagnetic tomography imaging.

19. At least one non-transitory computer-readable storage medium having stored thereon instructions that, when executed by at least one processor of a brain monitoring apparatus, cause the at least one processor to execute the steps of claim 1.

* * * * *